United States Patent [19]

Christel et al.

[11] Patent Number: 5,433,751
[45] Date of Patent: Jul. 18, 1995

[54] BONE PROSTHESIS MATERIAL CONTAINING CALCIUM CARBONATE PARTICLES DISPERSED IN A BIORESORBABLE POLYMER MATRIX

[75] Inventors: Pascal Christel, Paris; Su M. Li, Montpellier; Michel Vert, Mont Saint-Aignan; Jean-Louis Patat, Paris, all of France

[73] Assignee: INOTEB, Saint Gonnery, France

[21] Appl. No.: 41,173

[22] Filed: Apr. 1, 1993

[30] Foreign Application Priority Data

Apr. 3, 1992 [FR] France .................. 92 04096

[51] Int. Cl.⁶ .............................................. A61F 2/28
[52] U.S. Cl. ......................................... 623/16; 623/11; 623/66; 623/901; 606/77
[58] Field of Search ................... 623/11, 16, 66, 901; 604/266; 606/77

[56] References Cited

U.S. PATENT DOCUMENTS

| 3,739,773 | 6/1973 | Schmitt et al. |
| 3,867,190 | 2/1975 | Schmitt et al. |
| 4,356,572 | 11/1982 | Guillemin et al. | 606/77 |
| 4,595,713 | 6/1986 | St. John | 623/16 |
| 4,612,923 | 9/1986 | Kronenthal | 606/77 |
| 4,722,948 | 2/1988 | Sanderson . |
| 4,938,763 | 7/1990 | Dunn et al. | 604/890.1 |
| 4,976,736 | 12/1990 | White et al. | 606/77 |
| 5,007,930 | 4/1991 | Dorman et al. | 623/16 |
| 5,084,051 | 1/1992 | Tormala et al. | 623/16 |

FOREIGN PATENT DOCUMENTS

| 2070153 | 9/1971 | France . |
| 2364644 | 4/1978 | France . |
| 2439003 | 5/1980 | France . |
| 2460657 | 1/1981 | France . |

*Primary Examiner*—Paul Prebilic
*Attorney, Agent, or Firm*—Oliff & Berridge

[57] ABSTRACT

Bioresorbable bone prosthesis material containing particles of calcium carbonate, originating, for example, from coral skeleton, dispersed within a polymer matrix, the said particles being smaller than 1 mm in size and representing from 40 to 70% of the total weight, and the said polymer being a bioresorbable polymer.

23 Claims, No Drawings

BONE PROSTHESIS MATERIAL CONTAINING CALCIUM CARBONATE PARTICLES DISPERSED IN A BIORESORBABLE POLYMER MATRIX

The present invention relates to a bioresorbable bone prosthesis material containing calcium carbonate particles dispersed within a bioresorbable polymer matrix.

It is known that some polymers, such as aliphatic polyesters, and especially those derived from lactic and glycolic acids, have been recommended as bioresorbable materials, for example in surgery, for the production of suture threads or of osteosynthesis items (see, for example, U.S. Pat. Nos. 3,739,773 and 3,867,190 and Patents FR 2,364,644 and 2,439,003), or alternatively in pharmacology for the production of a system for the controlled release of active principles (see, for example, Patent FR 2,070,153). They are bioresorbable synthetic polymers, that is to say they are gradually degraded in the body and eliminated via the natural routes. Their degradation products, for example lactic and glycolic acids, are normal metabolites and are hence fully tolerated by the living milieu.

In Patent FR 2,460,657, the use has been described of calcium carbonate, in particular in the form of solid items, in the production of biodegradable implants which can be used as bone prosthesis items. Such implants, produced, for example, from skeletons of natural coral, are well-tolerated, and their gradual degradation takes place to the benefit of a regrowth of the bone tissue.

One of the drawbacks of prosthesis items based on calcium carbonate is the difficulty of shaping them, which can necessitate intricate machining in the case of complex shapes.

Moreover, a drawback of the abovementioned polyesters of hydroxy acids is that their rate of degradation is difficult to control. This rate of degradation is generally too slow in the case where the polymers are in the crystalline state, and is often too fast when the polymers are in the amorphous state.

In addition, it has been discovered that the degradation is faster inside the polymer material than at the surface, which can dangerously weaken the implanted prosthesis item.

In Patent FR 2,364,644, the use had been described, more especially, of crystalline polymers with the introduction into the polymer material of a filler (calcium phosphate) present in the proportion of 0.5 to 30% by weight, and preferably 0.5 to 5% by weight, so as to facilitate the resorption of the polymer. The suggested mechanism was that the presence of the filler makes microheterogeneities in the polymer bulk, facilitating attack at certain points of the polymer material and hence modifying its capacity for resorption. In other words, the particles of the filler were considered to constitute preferential points of attack of the surface of the polymer, with the formation of microcavities favourable to the development of neoformed bone tissue.

It has now been discovered that, surprisingly, the combination of calcium carbonate particles with the abovementioned biodegradable polymers enables the rate of resorption of the polymer to be decreased, in contrast to what was observed in the case of a calcium phosphate-based filler in Patent FR 2,364,644.

In addition, the properties of the polymer implant are considerably improved as a result of the incorporation of calcium carbonate particles, as is made clear in the experimental part below.

It has also been discovered that it is generally preferable to use amorphous polymers in the production of bone prosthesis items.

Calcium carbonate improves the properties of the implant, even when the polymer material is a crystalline material.

As a result of the combination of large amounts of particulate calcium carbonate with a polymer matrix, it is possible to obtain a composite material which has the same advantages as the calcium carbonate-based materials without having their drawbacks, that is to say the difficulty of producing items of any particular shape.

The subject of the present invention is hence a bioresorbable bone prosthesis material containing calcium carbonate particles dispersed within a polymer matrix, the said particles being smaller than 1 mm in size and representing from 40 to 70% of the total weight, and the said polymer being a bioresorbable polymer.

The polymers which can be used according to the invention are, of course, biocompatible polymers, that is to say polymers which can be implanted in man or in vertebrate animals without causing unacceptable side effects in the body. Such polymers are well known, many representatives having been described in the literature.

Among the polymers which can be used, special mention will be made of polymers in which the units are derived from hydroxycarboxylic acids. These polymers are hence polyesters, but are sometimes designated in the present application by the name "hydroxy acid polymers".

These polymers can be homopolymers or copolymers.

Preferably, amorphous polymers are used.

Among the polymers which can be used in the production of the material according to the invention, poly(lactic acids) originating from the polymerisation of mixtures of L- and D-lactides in proportions such that the said poly(lactic acids) are amorphous will be mentioned more especially. These polymers consist of a mixture of units derived from D- and L-lactic acids. It is possible to use, in particular, a poly(lactic acid) containing from 20 to 80%, and especially from 30 to 70%, expressed in terms of units, of D-lactic units. It is possible to use, in particular, a poly(lactic acid) containing equal proportions of the units derived from D-and L-lactic acids.

Among the copolymers which can be used, special mention may be made of copolymers consisting of units derived from lactic and glycolic acids, and for example a copolymer containing up to 50%, expressed in terms of units, of units derived from glycolic acid. With more than 50% of glycolic units, the copolymers are difficult to purify since they become insoluble in the common solvents.

When the prosthesis item is intended for replacing bone parts which undergo relatively large stresses, it must have adequate mechanical properties. In general, the polymer should have a sufficiently high average molecular mass, for example a weight average molecular mass equal to at least approximately 40,000, for the material of the invention to be capable of withstanding the mechanical stresses to which it has to be subjected after implantation. The choice of molecular mass may hence be determined in each case by routine experiments.

When the prosthesis item is an infilling item which does not undergo large mechanical stresses, it is possible to use the polymer material in the form of a pasty product which can be readily placed in position as a result of its capacity for being shaped. The pasty material may be obtained by using amorphous polymers of low average molecular mass, or by using a mixture of amorphous polymers of high and low average molecular masses. For example, it is possible to obtain pasty polymers or copolymers, in particular by mixing an amorphous poly(lactic acid) of high average molecular mass, for example greater than 20,000, with an amorphous poly(lactic acid) of low average molecular mass (especially less than 10,000, or less than 5,000), the latter polymer playing the part of a plasticizer. The proportion of low molecular mass poly(lactic acid) may be, in particular, a sufficient proportion for the glass transition temperature of the polymer mixture to be below a predetermined temperature, especially below 50° C., for example below 37° C. In effect, the glass transition temperature decreases as the proportion of low molecular mass polymer increases.

The fluidity of the paste, which increases with the content of low molecular mass poly(lactic acid), can be adjusted. In this case also, the composition of the polymer mixture may be determined by simple routine experiments.

The abovementioned polymers are known or may be prepared according to known methods. Some of them are, moreover, commercially available products. For example, to prepare a poly(lactic acid) of high average molecular mass, or a lactic/glycolic copolymer, it is possible to proceed by a ring-opening of the cyclic diester (lactide, glycolide) according to standard methods. To prepare a low molecular mass poly(lactic acid), it is possible to proceed, in particular, by polycondensation of mixtures of L- and D-lactic acids, for example DL-lactic acid. Corresponding copolymers are prepared in a similar manner.

The molecular masses of the polymers used according to the invention may be determined, for example in solution by gel permeation chromatography, by comparison with reference polymers (for example polystyrene).

The material of the invention can contain calcium carbonate in crystalline form (aragonate and/or calcite). The calcium carbonate may be obtained from any natural or synthetic, porous or non-porous material containing calcite or aragonite.

Among aragonite-based materials, those consisting of coral skeleton will be mentioned in particular. For example, skeleton of madreporic coral such as Porites, Pocillopora or Favites may be used.

It is also possible to use the shells of certain molluscs or bivalves, for example Pinctada margaritifera.

The calcite-based materials can consist, in particular, of echinoderm skeletons, especially sea urchin skeletons, or alternatively sea urchin spines.

The coral or echinoderm skeletons may be cut into sections and then subjected to a grinding and, where appropriate, to a sieving to obtain particles of the desired sizes. The particles may then be subjected to a treatment that enables the organic residues to be removed, for example by immersion in sodium hypochlorite solution for 48 h, then rinsed in running water and thereafter sterilised, for example using damp heat (120° C., 30 min).

To prepare the material of the invention, it is possible to proceed by mixing the polymer constituting the matrix, in powder or paste form, with the calcium carbonate powder.

It is also possible to proceed by adding the calcium carbonate powder to a solution of the polymer in an organic solvent, after which the solvent is evaporated off with stirring. The solvent (for example acetone) is then evaporated off gradually with stirring. The residual solvent may then be removed in a vacuum oven. The solid mixture obtained may then be compression molded at a temperature at least equal to the softening temperature of the polymer.

It is also possible to subject the solid mixture obtained to a grinding so as to obtain the material of the invention in powder form. The powder obtained, which has, for example, particle sizes of 50–500 $\mu$m, may then be made into the desired shape by moulding.

The moulded solid items can, in addition, be machined to give them substantially the shape of the bone fragment they are designed to replace.

The material of the invention may be used in bone surgery, including dental surgery (for example for the production of artificial roots for teeth).

The material of the invention in powder form may also be used to coat, by molding, solid items made of inert material, such as the femoral shank of a hip prosthesis, thereby permitting temporary attachment, by force fitting, into the medullary cavity, and then promoting permanent attachment by stimulation of bone regrowth in contact with the implant. This coating of a prosthesis enables the acrylic cement interface generally used, which constitutes the major source of the loosenings observed in this type of procedure, to be replaced.

The subject of the invention is also the bone prosthesis items formed totally or partially on the basis of the material of the invention.

The subject of the invention is also the use of calcium carbonate particles dispersed within a polymer matrix in the preparation of a bone prosthesis item, the said particles being smaller than 1 mm in size, and the said polymer being a bioresorbable polymer as defined above.

The subject of the invention is, in addition, a process for improving the properties of bone prostheses containing a biodegradable polymer, by incorporation of calcium carbonate in a matrix of the said polymer which is as described above.

It is, of course, possible to incorporate other common active ingredients in particulate form, for example antibiotics, in the polymer matrix.

The examples which follow illustrate the invention without, however, limiting it.

EXAMPLE 1: Polymer synthesis, purification and characterisation

Poly(lactic acids) are designated by the name PLA X (X representing the percentage of units derived from L-lactic acid).

Lactic acid/glycolic acid copolymers are designated by the name PLA X GA Y, X representing, as before, the percentage of units derived from L-lactic acid and Y representing the percentage of units derived from glycolic acid in the mixture of starting monomers. The content of units derived from D-lactic acid in these polymers is hence (100-X-Y). The percentages here are percentages expressed in terms of units.

The polymers Nos. 1 and 2 are marketed by the company Phusis.

The polymer No. 3 was prepared by the ring-opening of DL-lactide (100 g), which was recrystallised in acetone and dried under vacuum (45° C.; 3 days). The polymerisation is performed at 140° C. for 8 days in the presence of 0.05% by weight of zinc powder. The crude polymer obtained is purified by dissolution in 500 ml of acetone, followed by precipitation by the gradual addition of ethanol. The precipitated polymer is dried under vacuum (40° C.; 8 days).

The polymers obtained commercially were subjected to a similar purification.

Characterisation of the polymers was performed by gel permeation chromatography (GPC) by comparison with polystyrene reference standards, the mobile phase being dioxane.

The molecular masses of the polymers prepared are given in Table I.

TABLE I

|  | Polymer No | | |
| --- | --- | --- | --- |
|  | 1 | 2 | 3 |
| Composition | PLA37.5 GA25 | PLA50 | PLA50 |
| $Mp(\times 10^{-3})$ | 63 | 136 | 228 |

EXAMPLE 2: Production of coral/polymer mixtures

The coral, in powder form, is that marketed by the company Inoteb under the name Biocoral (particle size: 300–450 μm).

a) Mixing in air 4 g of the polymer No. 1 are added to 18 ml of acetone and the mixture is stirred until the solid has dissolved. 6 g of coral powder are then added. While the mixture is kept stirring, the solvent is gradually evaporated off. The mixture is then dried in a vacuum oven at 40° C. to remove the residual solvent.

The mixture was compression moulded in the following manner: the mould is placed on the heated platen (150° C.) of a press. After 30 minutes, when the mould has reached an equilibrium temperature of approximately 132° C., the mixture is introduced into the mould and heated for 10 minutes. A pressure of 100 bars ($10^7$ Pa) is then applied, and the mould is thereafter rapidly cooled with cold running water for 10 minutes. After the cold mould is opened, a plate 75 mm in diameter and 1.2 mm in thickness is obtained.

A cylinder 14 mm in diameter and 9 mm in height was prepared in the same manner.

Plates and cylinders were prepared in a similar manner with the polymers No. 2 and No. 3 and a proportion of coral equal, as above, to 60%.

b) Mixing under vacuum 2 g of the polymer No. 2 and 10 ml of acetone are mixed in a round-bottomed flask connected to a rotary evaporator. When the vacuum is established, 3 g of coral are introduced into the solution. The flask is kept rotating slowly to obtain a homogeneous mixture while the solvent is gradually evaporated off. The mixture is then dried in a vacuum oven at 40° C. for 24 h. With this mixture a plate and a cylinder were prepared by moulding, as above.

It is found that, for the same mass of polymer and of coral, the mixture prepared under vacuum is smaller in volume than the mixture prepared in air. The explanation of this phenomenon is that the coral used here as a source of calcium carbonate is porous.

In vitro degradation

The plates obtained above were cut into small test pieces 12 mm × 12 mm approximately. Each test piece was introduced into a bottle filled with 30 ml of phosphate buffer (pH=7.4). The bottles are placed in an oven at 37° C. At each time interval, some test pieces are removed, rinsed, dried and analysed.

A comparison was made, in particular, of test pieces originating from a plate produced as above with the polymer No. 3 alone (without coral), and with the polymer No. 3 and coral (mixture containing 60% by weight of coral). Test pieces of the same weight were compared.

In the first place, it was noted by visual inspection that PLA50 test pieces swelled greatly and became misshapen during degradation, whereas those of the coral/PLA50 mixture retained the same shape and size.

For PLA50, the absorbed water content increased very quickly and reached a value of 176% after 10 weeks (swelling of the test pieces). In the case of the coral/PLA50 mixture, the absorbed water content was greater (approximately 40%) than for PLA50 after one week of degradation, but the absorbed water content then increased no further: it even tended to decline, amounting to less than 30% after 25 weeks.

For PLA50, there was no detectable loss of mass before 10 weeks. Between 10 and 17 weeks a big loss (73%) was observed. After this, the test pieces went on losing mass, but more slowly. In contrast, the case of the coral/PLA50 mixture is very different. After one week, a small loss of 2% is detected. Subsequently, the loss of mass increased only very slightly, reaching 3 or 4% after 25 weeks.

The changes in the concentration of L-lactic acid detected in the degradation medium were also studied. These changes conform exactly to the changes in the loss of mass. With PLA50, no L-lactic acid is detected for up to 10 weeks. Between 10 and 17 weeks, a large increase in the L-lactic acid concentration was observed. After this, this increase slowed down. For the PLA50/coral mixture, the lactic acid concentration is approximately one fifth the value (17 weeks) and one tenth the value (25 weeks) observed in the case of PLA50 alone.

In conclusion, the incorporation of coral slows down the degradation of polymer and modifies the features of this degradation.

What is claimed is:

1. Bioresorbable bone prosthesis material containing calcium carbonate particles dispersed within a polymer matrix, said particles being smaller than 1 mm in size and representing from 40 to 70% of the total weight, and said polymer matrix comprising an amorphous hydroxy acid polymer that is bioresorbable.

2. Material according to the claim 1 wherein said polymer is a lactic acid polymer.

3. Bioresorbable bone prosthesis material containing calcium carbonate particles dispersed within a polymer matrix, said particles being smaller than 1 mm in size and representing from 40 to 70% of the total weight, and said polymer matrix comprising a bioresorbable and amorphous polymer that is a poly(lactic acid) consisting of a mixture of units derived from D- and L-lactic acids, the proportions of each of the D and L units being sufficient for the said poly(lactic acid) to be amorphous.

4. Material according to the claim 3 wherein said poly(lactic acid) contains from 30 to 70% of D-lactic units.

5. Material according to the claim 4 wherein said poly(lactic acid) contains equal proportions of the units derived from D- and L-lactic acids.

6. Material according to claim 1 wherein said polymer is a copolymer.

7. Material according to claim 6 wherein said copolymer is a copolymer containing units derived from lactic acids and from glycolic acid.

8. Material according to the claim 7 wherein said copolymer contains up to 50%, expressed in terms of units, of units derived from glycolic acid.

9. Material according to claim 1 wherein said polymer has a sufficiently high average molecular mass for the material to be capable of withstanding the mechanical stresses to which it has to be subjected after implantation.

10. Material according to claim 9 wherein said polymer has a weight average molecular mass equal to at least approximately 40,000.

11. Material according to claim 1 wherein said polymer has a sufficiently low average molecular mass for the material to take the form of a pasty solid at a temperature below 50° C.

12. Material according to claim 11 wherein said polymer contains at least partially of a polymer having a weight average molecular mass of less than 10,000.

13. Material according to claim 1 wherein said material contains from 50 to 70% by weight of calcium carbonate.

14. Material according to claim 1 wherein said calcium carbonate is in the form of calcite or aragonite.

15. Material according to claim 1 wherein said calcium carbonate is obtained from calcium carbonate-based marine organism skeletons, from mollusk or from bivalve shells.

16. Material according to claim 15 wherein said calcium carbonate is obtained from coral skeletons, from sea urchin skeletons or spines from sea urchin from Pinctada margaritifera shells.

17. Material according to claim 1 wherein said material takes the form of a moldable powder or the form of a molded solid item.

18. A method of preparing a bone prosthesis item, comprising forming a bone prosthesis item from a material comprising calcium carbonate particles dispersed within a polymer matrix, said particles being smaller than 1 mm in size, and said polymer being a bioresorbable and amorphous polymer comprising a hydroxy acid polymer.

19. A method according to claim 18, wherein said particles constitute from 40% to 70% of a total weight of said material.

20. Material according to claim 11, wherein said polymer has a sufficiently low average molecular mass for the material to take the form of a pasty solid at a temperature below 37° C.

21. Material according to claim 12, wherein said polymer contains at least partially of a polymer having a weight average molecular mass of less than 5,000.

22. Bioresorbable bone prosthesis material containing particles consisting essentially of calcium carbonate dispersed within a polymer matrix, said particles being smaller than 1 mm in size and representing from 40 to 70% of the total weight and said polymer being a bioresorbable amorphous and hydroy acid polymer.

23. A method of controlling the rate of degradation of a resorbable and amorphous hydroxy acid polymer comprising adding calcium carbonate particles to said hydroxy acid polymer, said particles having a size of less than 1 mm and representing an amount of 40–70% of the total weight.

* * * * *